United States Patent [19]

Dandreaux et al.

[11] Patent Number: 4,981,974

[45] Date of Patent: Jan. 1, 1991

[54] POLYMERIZABLE PYRROLIDONYL OXAZOLINE MONOMERS

[75] Inventors: Gary . Dandreaux, Bloomfield; Robert B. Login, Oakland; John J. Merianos, Middletown; Paul Garelick, South Plainfield; Krystyna Plochocka, Scotch Plains; Max Negrin, Bloomfield; Jenn S. Shih, Paramus, all of N.J.

[73] Assignee: GAF Chemicals Corporation, Wayne, N.J.

[21] Appl. No.: 495,061

[22] Filed: Mar. 19, 1990

Related U.S. Application Data

[62] Division of Ser. No. 349,362, May 8, 1989, Pat. No. 4,933,463.

[51] Int. Cl.$^5$ .................................... C07D 263/14
[52] U.S. Cl. .................................... 548/238; 523/122; 525/927; 548/531
[58] Field of Search ........................ 548/238, 239

[56] References Cited

U.S. PATENT DOCUMENTS 4,581,364 4/1986 Weber et al. .................. 548/531
4,857,528 8/1989 Weber et al. .................. 514/252

OTHER PUBLICATIONS

Zoretic et al. Synth. Commun. vol. 7 (No. 4) pp. 299–303 (1977).
"Polymerization of Cyclic Iminoethers. III. Effect of Ring Substituents", A. Levy and M. Litt, Journal of Polymer Science: Part A-1, vol. 6, pp. 57–62 (1968).
Synthetic Approaches to 10-Azaprostaglandins, P. A. Zoretic et al J. Org. Chem. 1980, 45, 810–814.
Synthesis of 11-Deoxy-8-Azaprostaglandin $E_1$, P. A. Zoretic et al. J. Org. Chem., 1977, vol. 42, No. 19, 3201–3203.

Primary Examiner—Donald G. Daus
Attorney, Agent, or Firm—Walter Katz; Marilyn J. Maue; Joshua J. Ward

[57] ABSTRACT

What is described herein are polymerizable pyrrolidonyl 4,5-unsubstituted oxazoline monomers, homopolymers thereof, and copolymers with other monomers. A preferred polymerizable monomer compound is 2-(1-methyl-2-pyrrolidon-4-yl)-2- oxazoline. The polymers herein have excellent hydrotropic properties thus increasing the water solubility of organic compounds previously considered as water insoluble, and exhibit complexation with water soluble consolutes.

2 Claims, No Drawings

POLYMERIZABLE PYRROLIDONYL OXAZOLINE MONOMERS

This is a division of application Ser. No. 349,362, filed May 8, 1989, now U.S. Pat. No. 4,933,463.

BACKGROUND OF THE INVENTION

1. Field of the Invention

This invention relates to pyrrolidonyl oxazoline compounds, and more particularly, to polymerizable pyrrolidonyl 4,5-unsubstituted oxazoline monomers, homopolymers thereof having advantageous complexation and solubilization properties, and copolymers with other monomers.

2. Description of the Prior Art

Polyvinylpyrrolidone (PVP) is a well known synthetic polymer having properties which are suitable for many pharmaceutical, cosmetic, clinical and industrial uses. An important property of PVP is an ability to form complexes with a variety of compounds, such as iodine, phenolic materials, dyes etc.

Other useful properties of PVP include water solubility, adhesion to many substrates, suspending and emulsifying capabilities, relative inertness, ability to form clear brittle films from various solvents, and its non-toxicity.

However, PVP is not without its deficiencies. Some of these include a high glass transition temperature, Tg, of 175° C. and a high melt viscosity, which preclude its use in thermoplastic forming operations; an amorphous structure; non-biodegradability, which prevents complete elimination from the body after intravenous administration; and steric crowding between the pyrrolidone lactam ring and the hydrocarbon backbone of the polymer which limits its complexation with other molecules when dipole-dipole interactions are involved.

Accordingly, it is an object of the present invention to provide new and improved pyrrolidone-containing polymers.

The literature has disclosed two pyrrolidonyl 4,4'-dimethyl substituted oxazoline compounds for use as an intermediates in the synthesis of medicinal drugs [Zoretic, P.A. *J. Org. Chem.* 45, No. 5, 810-814 (1980) and Zoretic, P.A. *J. Org. Chem.* 42, No. 19, 3201-3203 (1977)]. However, the presence of the dimethyl substituent group in the oxazoline ring is known to preclude its polymerization into polymeric materials [Levy, A. *J. Poly. Sci* Part 1-A 6, 57-62 (1968)].

Accordingly, it is another object of this invention to provide polymerizable monomers of pyrrolidonyl oxazolines, and homopolymer and copolymers thereof.

A particular object herein is to provide a polymerizable pyrrolidonyl 4,5-unsubstituted oxazoline monomer and a homopolymer thereof having a lactam ring which is spaced away from the hydrocarbon backbone of the polymer, thus avoiding the steric crowding deficiency of PVP.

Still another object of the invention is to provide pyrrolidonyl oxazoline polymers having two amide moieties per repeat unit to enhance its complexation properties.

Among the other objects herein is to provide advantageous processes for the homopolymerization and copolymerization of the monomer compounds of the invention.

SUMMARY OF THE INVENTION

What is provided herein are:

A. Polymerizable Monomers

Pyrrolidonyl 4,5-unsubstituted oxazolines having the formula:

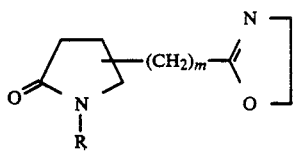

where m is 0 to 4 and R is hydrogen or lower alkyl; preferably m is 0 and R is methyl; e.g. 2-(1-methyl-2-pyrrolidon-4-yl)-2-oxazoline; or

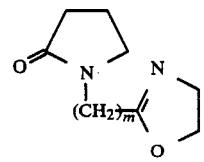

where m is 0-4; e.g., 1-[(2-oxazolin-2-yl)methyl]-2-pyrrolidone, where m=1.

B. Homopolymers of A

Pyrrolidonyl 4,5-unsubstituted oxazolines are polymerized to form homopolymers having the formula:

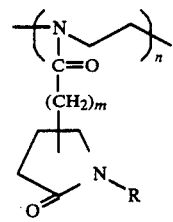

where n is an integer having a value of from 10 to 50,000; or

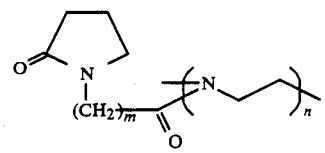

where n is as defined above.

C. Copolymers of A with Comonomers

Comonomers are copolymerized with pyrrolidonyl 4,5-unsubstituted oxazoline monomers to provide useful copolymers.

D. Properties

The polymers of the invention have (1) excellent hydrotropic properties thus increasing the water solubility of many drugs and other organic compounds previously considered as water insoluble;

(2) effective complexation properties with iodine, phenolic and carboxylic acid compounds; and (3) water solubility.

DETAILED DESCRIPTION OF THE INVENTION

In accordance with the present invention, there is provided herein polymerizable pyrrolidonyl 4,5-unsubstituted oxazoline monomers, homopolymers and copolymers.

1. Polymerizable Monomers

The monomer compounds of the present invention are readily synthesized by a commercially feasible and economic process. In general, the process comprises condensing pyrrolidone carboxylic acids (I) and (II) with ethanolamine (III) to form the corresponding hydroxyamide intermediates (IV) and (V), respectively, which in turn are cyclodehydrated to form the desired oxazoline monomers (VI) and (VII), respectively.

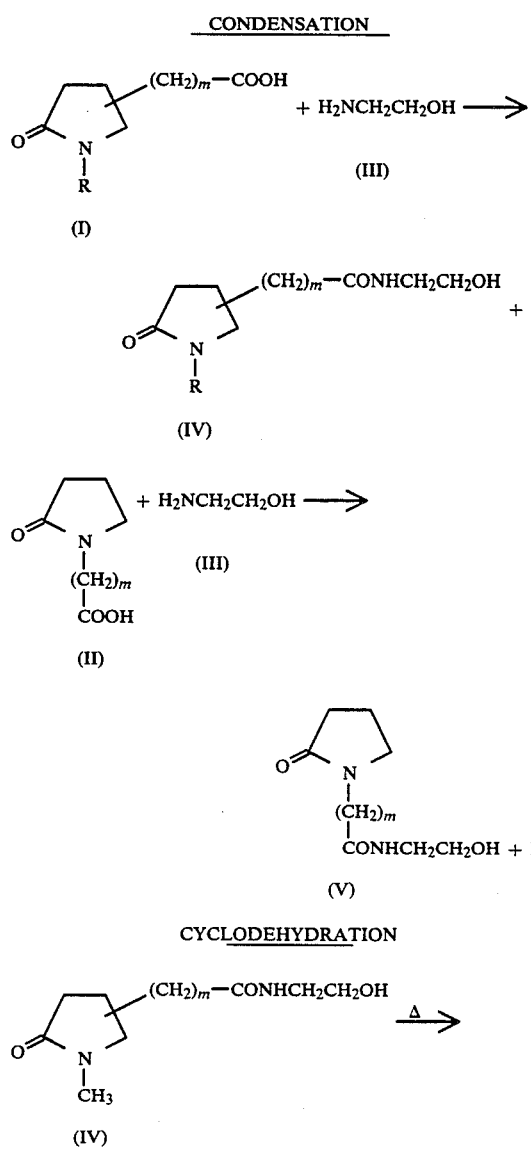

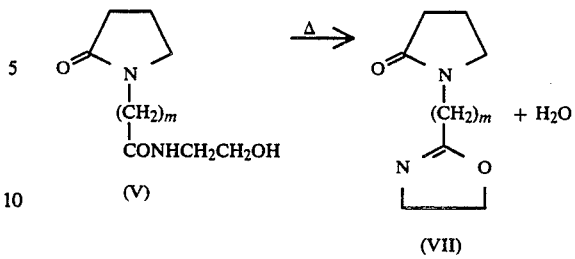

In the case of 2-(1-methyl-2-pyrrolidon-4-yl)-2-oxazoline the starting material (I) (R=CH$_3$, m=0) is provided by reaction between itaconic acid and methyl amine and elimination of water.

The above reactions can be conveniently carried out in a one-pot synthesis. The condensation reaction is carried out at a temperature of about 70°–150° C. under atmospheric pressure or pressures up to about 500 psig for a period of about 10–20 hours. Cyclodehydration is effected at a pot temperature of about 230°–260° C. (vapor temperature of about 110°–170° C.) under reduced pressure.

Although these reactions can be effected in the absence of a solvent, it is recommended that an inert liquid, such as xylene, toluene or other inert liquid be employed. These solvents form an azeotrope with water which is utilized to remove the by-product in order to increase the overall yield of the reaction.

In a similar manner, pyroglutamic acid, i.e. 5-oxo-2-pyrrolidinecarboxylic acid, where R=H and m=O in the above formula (I), can be condensed with ethanolamine and cyclodehydrated to form the corresponding monomer 2-(2-pyrrolidon-5-yl)-2-oxazoline.

1-[(2-oxazolin-2-yl)methyl]-2-pyrrolidone, for example, can be obtained by condensation of pyrrolidone and chloroacetic acid to form 2-pyrrolidone acetic acid, where m =1 in the above formula (II), or, alternatively, by condensing butyrolactone with glycine, and the starting carboxylic acid condensed with ethanolamine and cyclodehydrated to form 1-[(2-oxazolin-2-yl)methyl]-2-pyrrolidone.

2. Homopolymers

A. Preparation

The pyrrolidonyl 4,5-unsubstituted oxazoline monomer (VI) can be homopolymerized to form polymer (VIII), as shown below:

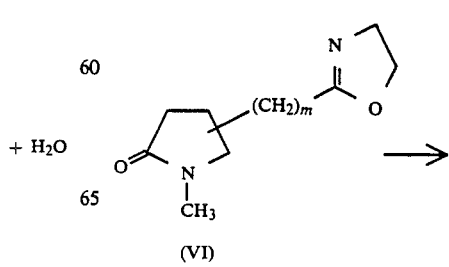

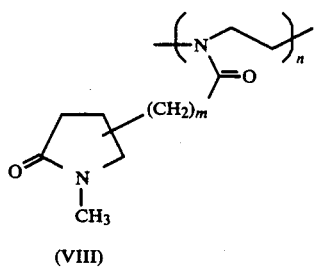

(VIII)

The polymerization reaction is carried out cationically with an initiator such as an alkyl halide, a boron-fluorine compound, a antimony-fluorine compound, an oxazoline salt of a strong acid, a strong acid or an ester of a strong acid. Typical polymerization initiators include dimethyl sulfate and methyl p-toluenesulfonate. In general, the polymerizations of the present invention are carried out in solutions of (VI) and the initiator at a temperature between about 60° C. and 170° C.

The following polymerization can be carried out in a similar manner.

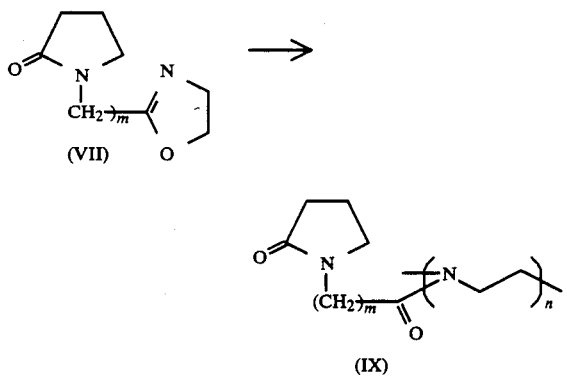

B. Structure

The polymers of the invention are characterized by a pendant pyrrolidonyl group which is spaced away from the backbone of the polymer, and two amide groups per repeat unit. One amide group comes from the oxazoline ring; its nitrogen atom is included in the polymer backbone, while its carbonyl group is located outside the backbone and is available for hydrogen bonding with other compounds or ions. The second amide group is present in the pyrrolidonyl ring, and it is sterically unhindered and is available for dipole-dipole interactions and hydrogen bonding.

C. Properties

The polymers of this invention have a number average molecular weight ranging between about 1,600 and about 8,500,000, preferably about 10,000 and 100,000 depending upon the catalyst, and reaction temperature and time.

The polymeric products of this invention form complexes with a wide variety of components including phenolics and other compounds having an acidic hydrogen, such as benzoic acid and salicylic acid. Insoluble compounds are rendered water soluble through the formation of complexes with the present polymers, and toxic compounds, in the complexed form, become less irritating.

Having thus generally described the invention, reference is now had to the accompanying examples which set forth preferred embodiments but which are not to be construed as limiting to the scope of the invention as more broadly defined above and in the appended claims.

EXAMPLE 1

Preparation of 2-(1-Methyl-2-Pyrrolidon-4-yl-)-2-Oxazoline Monomer (MPO)

A. Starting Material

A 5-liter, 4-necked flask equipped with stirrer, cooling (ice water) bath, addition funnel, thermometer, and dry ice condenser was charged with 1310 g. (10.1 mol) of itaconic acid, and 1500 ml. of xylene. Then 800 g. of a 40% aqueous methylamine solution was added dropwise with stirring over a one-hour period while keeping the temperature between 22° and 28° C. The reaction mixture was then stirred for 12 hours at room temperature. The reaction flask was then fitted with a Deal-Stark receiver, reflux condenser and electric heating mantle, and a total of 661 g. of water (660 g. expected) was removed azeotropically over a period of 13 hours. During this period, the reflux temperature rises to 135° C. from 104° C. The reaction product was subjected to GC analysis which indicated that 1-methyl-5-oxo-3-pyrrolidinecarboxylic acid was the major product.

B. Condensation

The flask then was cooled to 115° C. and 763 g. (12.5 mol) of ethanolamine was added gradually over about 1.5 hrs. with stirring. Upon completion of the addition, the solution was left overnight. 260 ml. of an expected 360 ml. water was removed azeotropically over a 12-hour period. 360 ml. of water is the total expected for complete conversion to the oxazoline.

C. Cyclodehydration

The xylene was distilled off at atmospheric pressure and the temperature of the pot was allowed to rise to 155° C. Part of this crude material (685 g.) was vacuum distilled (230°-260° C., 0.1 mm Hg) to yield 241 g. of MPO (liquid; 91% purity).

EXAMPLE 2

Polymerization of MPO

Preparation of Poly[2-(I-Methyl-2-Pyrrolidon-4-yl)-2-Oxazoline](P-MPO)

A charge of 20 ml. of MPO and 0.044 g. of methyl-p-toluenesulfonate was prepared under a nitrogen atmosphere. Then the reaction mixture was added to a tube which was sealed off under vacuum. The tube was then heated according to the following schedule:

| Temperature (°C.) | Time (hr.) |
| --- | --- |
| 60 | 16 |
| 70 | 24 |
| 80 | 30.5 |
| 90 | 41.5 |
| 100 | 8 |
| 110 | 15 |
| 120 | 8 |
| 130 | 17 |
| 140 | 8 |
| 150 | 15.5 |
| 160 | 24 |
| 170 | 8 |

The solid polymer obtained had a relative viscosity in water (1% solution, 25° C.) of 1.63. The absolute molecular weight of the material, as determined by vapor phase osmometry, was 12,100 and Tg was 150° C.

EXAMPLE 3

Copolymerization of MPO Copolymers with 2-Ethyl-2-Oxazoline

A one-liter flask equipped with a condenser and a nitrogen purge was charged with 100 g. of MPO (purity greater than 99%, as determined by GC), 100 g. of 2-ethyl-2-oxazoline, 400 g. of N-methylpyrrolidone solvent, and methyl p-toluenesulfonate initiator (5001 molar ratio of MPO to initiator). The reaction mixture then was heated at 100° C. for 20 hours and then at 130° C. for 6.5 hours. At this point, no further change in the infrared spectrum of the mixture was noted. The copolymer product was isolated by precipitation with diethyl ether. The polymer has a relative viscosity in water of 1.38 (1% aqueous solution at 25° C.).

The copolymer exhibited solubility properties in organic solvents (ethanol, acetonitrile, methylene chloride, chloroform, ethyl acetate, 2-butanone and acetone) between those shown by its component homopolymers. Accordingly, a homopolymer of 2-ethyl-2-oxazoline (PEOX 50 - Dow) (relative viscosity in water of 1.38) was soluble, while PMPO was insoluble, in these solvents. A 50:50 mixture of the two homopolymers also was insoluble in the listed solvents. The copolymer, on the other hand, was soluble in ethanol, acetonitrile, methylene chloride and chloroform and insoluble in ethyl acetate, 2-butanone and acetone.

EXAMPLE 4

Complexation of PMPO with Organic Compounds

1. Phenol

The extent of complexation of phenol by PMPO was measured as a percent change of phenol absorbance, A, at 277 nm. The tests solutions were prepared from 25 ml. of 0.5% aqueous phenol in 25 ml. of water saturated heptane with and without 2.5 g. of polymer. The absorbance in the case of the sample containing polymer was corrected by subtracting the absorbance of a mixture containing 25 ml. water, 25 ml. water-saturated heptane and 2.5 g. polymer. The test solutions were agitated until undissolved polymer was no longer visible (1 hour). The phases were allowed to separate overnight. The polymer has a negligible solubility in the heptane layer. 1 ml. of the heptane layer then was diluted with 10 ml. of water-saturated heptane and its absorbance at the phenol band of 277.5 nm was measured. The % decrease in phenol absorbance upon addition of polymer is calculated.

The results are summarized below.

| Test No. | Test Solution | Corrected Absorbance A | % Decrease in A |
|---|---|---|---|
| 1 | phenol/ heptane | 0.965 | — |
| 2 | phenol/ heptane/ PMPO | 0.507 | 47.5 |
| 3 | phenol/ heptane/ PVP-30 | 0.530 | 44.0 |

These test results shown that the polymer of the invention exhibits a high degree of complexation with phenol and is somewhat higher than PVP itself.

2 Benzoic Acid

The above phenol experiment was repeated using 0.2% benzoic acid and absorbance was measured at 274 nm. The % decrease in absorbance of benzoic acid in the presence of PMPO (relative viscosity 1.54) was 58%. A control PVP C30 polymer also was 58%.

3. Salicylic Acid

The above phenol experiment was repeated using 0.2% salicyclic acid and absorbance was measured at 312 nm. The % decrease with PMPO (relative viscosity 1.54) was 86% whereas PVP C30 was only 83%.

4. Iodine 10 g. of PMPO polymer, 1.3333 g. of iodine and 0.8725 g. of potassium iodide were added to 87.7942 g. of water and stirred overnight. The weight ratio of total iodine to polymer was 0.2, and the weight ratio of molecular iodine to iodide was 2:1. The weight percentage of the polymer-iodine complex was 12% (neglecting potassium). The solution was filtered and 20.83 g. of solution was weighed out and diluted to 25 g. total with distilled water. One ml of sample solution was added to a 2 oz. bottle and 25 ml. of water-saturated heptane was added. The tests were performed in duplicate. The bottles were shaken vigorously for two minutes and the phases allowed to separate. The absorbance of the heptane phase at 515 nm ($I_2$) versus a water-saturated heptane blank (1 cm. cell) was determined on a Perkin-Elmer 559A UV/VIS spectrophotometer. The absorbance measurements were performed in duplicate. The results are shown below.

| SOLUTION | ABSORBANCE | |
|---|---|---|
| 1 | 0.252 | Average |
|   | 0.251 | Absorbance |
| 2 | 0.242 | = 0.248 |
|   | 0.246 | |

The same experiment was performed in the absence of PMPO. Upon filtration, insoluble iodine could be seen in the filter; this was not the case when polymer was present. Thus, PMPO in this instance acts to solubilize iodine. The absorbance of the heptane phase was 0.745; the presence of PMPO reduces the amount of $I_2$ which can be extracted showing complexation.

EXAMPLE 5

Solubilization of Furosemide by PMPO

Furosemide is a drug which is substantially insoluble in water at room temperature (0.06%). A 0.5% solution of the drug in 40% aqueous solution of PMPO (relative viscosity of 1.23) was observed to be clear at room temperature indicating solubilization of the insoluble compound by the polymer of the invention.

While the invention has been described with particular reference to certain embodiments thereof, it will be understood that changes and modifications may be made which are with the skill of the art. Accordingly, it is intended to be bound by the following claims only, in which:

What is claimed is:

1. A compound having the formula:

9
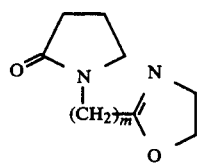
where m=0–4.
2. A compound according to claim 1 where m=1 which is 1-[(2-oxazolin-2-yl)methyl]-2-pyrrolidone.
* * * * *
10
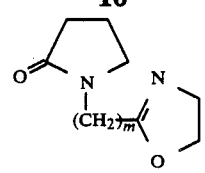
where m=0–4.
2. A compound according to claim 1 where m=1 which is 1-[(2-oxazolin-2-yl)methyl]-2-pyrrolidone.
* * * * *